United States Patent [19]

Morimoto et al.

[11] 3,957,836
[45] May 18, 1976

[54] QUINONE DERIVATIVES

[75] Inventors: Hiroshi Morimoto, Hyogo; Isuke Imada, Osaka; Masazumi Watanabe, Osaka; Mitsuru Kawada, Osaka, all of Japan

[73] Assignee: Takeda Chemical Industries, Ltd., Osaka, Japan

[22] Filed: June 28, 1974

[21] Appl. No.: 484,329

[30]  Foreign Application Priority Data
    July 2, 1973   Japan.............................. 48-74974
    Dec. 25, 1973  Japan.............................. 49-1519

[52] U.S. Cl............................ 260/396 R; 260/345.7; 260/345.8; 260/345.9; 260/473 F; 260/473 S; 260/479 R; 260/520 R; 260/521 R; 424/305; 424/308; 424/316; 424/317
[51] Int. Cl.² ................. C07C 66/00; C07C 69/95
[58] Field of Search ............................. 260/396 R

[56]    References Cited
        UNITED STATES PATENTS
3,728,362  4/1973  Morimoto et al. ............... 260/396 R
3,728,363  4/1973  Morimoto et al. ............... 260/396 R
3,849,453  11/1974 Morimoto et al. ............... 260/396 R Primary Examiner—Vivian Garner
Attorney, Agent, or Firm—Wenderoth, Lind & Ponack

[57]    ABSTRACT

Novel quinone derivatives of Formula

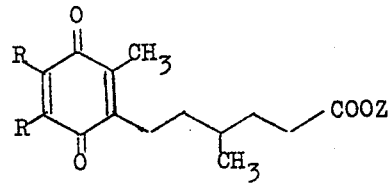

(wherein each R represents a lower alkyl group or a lower alkoxy group, or alternatively the R's, taken together, form -CH=CH-CH=CH-, and Z represnts hydrogen or a lower alkyl group) and pharmaceutically acceptable salts thereof exhibit excellent pharmacological activities such as vitamin-like activity, especially vitamin E-like activity, and immunosuppressive activity.

15 Claims, No Drawings

QUINONE DERIVATIVES

This invention relates to novel quinone derivatives. More concretely, this invention provides quinone derivatives of Formula [I]

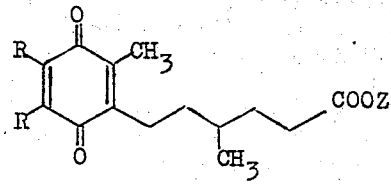

wherein each R represents a lower alkyl group or a lower alkoxy group, or alternatively the R's, taken together, form -CH=CH-CH=CH-, and Z represents hydrogen or a lower alkyl group, and their pharmaceutically acceptable salts.

The present inventors have made extensive studies on quinone derivatives to succeed in synthesizing the novel quinone derivatives of Formula (I) and found (1) that these compounds have excellent action to stabilize the lysosomal membranes of cells, vitamin-like activity, especially vitamin E-like activity and immunosuppressive activity, and accordingly, are of use as medicines; (2) that these compounds are invariably simple in chemical structure and easy to produce on an industrial scale; (3) that these compounds have an adequate degree of hydrophilicity and lend themselves conveniently to formulation into pharmaceutical products; and (4) that these compounds are eminently stable against acid and light and can be employed advantageously as medicines.

The present invention has been accomplished on the basis of these findings.

Thus, the principal object of this invention is to provide the novel quinone derivatives of Formula (I) and their pharmaceutically acceptable salts useful as medicines such as vitamin E-like medicines, immunosuppressive medicines and potentiators of immunosuppression. Another object of this invention is to provide an industrially feasible method for the production of these novel compounds, and a further object is to provide pharmaceutical composition comprising one or more of these compounds.

Compound (I) (throughout the present specification, the term "Compound" followed by Greek numerical notations (I through X) means the respective compounds of the corresponding Formulae) may be produced, for example, by oxidizing a compound of Formula (II)

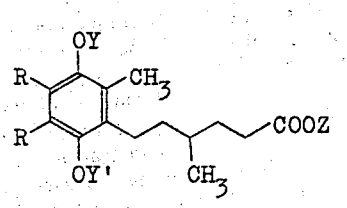

(wherein R's and Z have the same meaning as defined above and each of OY and OY' is a hydroxyl group which may be protected) (Process A), or by oxidizing a compound of Formula (III)

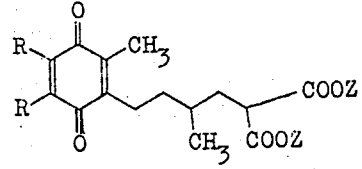

(wherein R's have the same meaning as defined above) (Process B), or by decarboxylating a compound of Formula (IV)

(wherein R's and Z have the same meaning as defined above) (Process C).

In Formulae [I] to [IV], the lower alkyl groups represented by R are preferably those having 1 to 4 carbon atoms, exemplified by methyl, ethyl, i-propyl, n-propyl, n-butyl, i-butyl.

The lower alkoxy groups, also represented by R, preferably those having 1 to 4 carbon atoms, exemplified by methoxy, ethoxy, i-propoxy, n-propoxy, n-butoxy, i-butoxy.

In Formulae (I), (II) and (IV), the lower alkyl groups represented by Z are preferably those having 1 to 4 carbon atoms, exemplified by methyl, ethyl, n-propyl, i-propyl, n-butyl, i-butyl, t-butyl.

OY and OY' in Formula (II), when they denote protected hydroxyl groups, may be the same or different groups. The protective group may be any type of group which can be easily removed. Among specific protective groups are alkoxy groups (e.g. methoxy, ethoxy, etc.), acyloxy groups (e.g. acetoxy etc.), acetals (e.g. alpha-tetrahydropyranyloxy etc.) and so on. These protected hydroxyls are oxidized to oxo groups by direct oxidation or by hydrolysis and subsequent oxidation.

Processes A to C will be more particularly mentioned below:

PROCESS A

In Process A, Compound (II) is oxidized to obtain Compound (I).

This oxidation reaction may be conducted with the employment of any agent capable of oxidizing hydroquinone to quinone. The preferred oxidizing agents are silver oxide, manganese dioxide, hydrogen peroxide, organic peracids (e.g. peracetic acid), dichromates, ferric chloride, oxygen, oxygen-containing gases (e.g. air), and the like. The reaction solvent varies with the type of oxidizing agent used, and mineral acids such as sulfuric acid, organic acids such as acetic acid, lower alcohols and water, among others, are suitable. Ordinarily the reaction proceeds at room temperature.

Compound (II) is highly susceptible to oxidation, and particularly Compound (II) wherein both OY and OY' are unprotected hydroxyl groups is readily oxidized, even when it is brought into contact with air in the isolation procedure, to give Compound (I). Therefore, after having been produced by the procedures of the step (2) to be described below Compound (II) is usually not isolated but directly subjected to Process A as it occurs in the reaction mixture.

In producing Compound (II) which is the starting material in Process A, an aliphatic chain is introduced into the phenyl nucleus. It is an established preferred practice to protect all or some of the hydroxyl groups on the phenyl nucleus prior to the introduction of said aliphatic chain. The starting material to be employed according to Process A may retain such protective groups.

When Z in Compound (II) is hydrogen, not only the free carboxylic acid but also the corresponding salt can be used in the oxidation reaction of this invention. The salt may be any type of salt insofar as it will not interfere with the reaction. Among specific such salts are alkali metal salts such as sodium and potassium salts; alkaline earth metal salts such as magnesium and calcium salts; and amine salts such as ammonium, trimethylamine and triethylamine salts.

PROCESS B

In Process B, Compound (III) is oxidized to obtain Compound (I).

This oxidation is performed by a procedure which is conventional, and any agent capable of oxidizing a hydroxyl group to a carboxyl group can be used as the oxidizing agent. Preferred examples of the oxidizing agents are permanganate (such as potassium permanganate); chromic acid and the like. The oxidation reaction of Process B may be conducted in the presence of a mineral acid such as sulfuric acid or hydrochloric acid, or a base such as pyridine. Depending upon the reaction conditions and the type of oxidizing agent, the reaction of the step (6) to be described below occurs in the first place and, then, the above-mentioned oxidation reaction takes place to give Compound (I).

PROCESS C

In Process C, Compound (IV) is decarboxylated to obtain Compound (I).

This reaction may be performed by a decarboxylation procedure which is conventional per se. For example, the decarboxylation of Compound (IV) may be achieved by heating Compound (IV), or a compound obtainable by hydrolytically removing the ester residue therefrom.

The heating temperature is ordinarily about 100°C to about 200°C and preferably about 140°C to about 160°C. In heating, use can be made of a suitable solvent according to the per se routine procedure.

The above-mentioned hydrolysis reaction may be advantageously conducted in the presence of, for example, a mineral acid (e.g. sulfuric acid, hydrochloric acid, etc.) or a base (e.g. sodium hydroxide, potassium hydroxide, calcium hydroxide, etc.). It should of course be understood that the hydrolysis is not essential even when Z in Compound (IV) is a lower alkyl group.

When Z in Compound (I) obtained by Process A, B or C is hydrogen, the compound can be esterified, by a procedure known per se, to Compound (I) in which Z is a lower alkyl group. The advantageous esterification procedures are those in which compound (I) wherein Z is hydrogen or a reactive derivative at the carboxyl function of said compound is reacted with alcohols, alkyl halide, dialkyl sulfate, diazomethane, and the like.

Examples of the reactive derivatives at the carboxyl function of said compound include the corresponding carboxylic acid anhydride, carboxylic acid halide, carboxylic acid lower alcohol esters, carboxylic acid metal salts such as sodium, potassium, silver, etc. salts. The alcohols may for example be methanol, ethanol, n-propanol, i-propanol, n-butanol, i-butanol, t-butanol, etc. The alkyl halide may for instance be methyl iodide or ethyl iodide.

When Z in Compound (I) obtained by Process A or C is a lower alkyl group, it can be converted to Compound (I) wherein Z is hydrogen by a hydrolytic procedure which is conventional per se. The above hydrolysis reaction is conducted with advantage in the presence of, for example a mineral acid (e.g. sulfuric acid, hydrochloric acid, etc.) or a base (e.g. sodium hydroxide, potassium hydroxide, calcium hydroxide, etc.).

Compound (I) produced by whichever of Processes A, B and C can be easily isolated by procedures conventional per se, for example, by such suitable procedures as phasic transfer, concentration, chromatography, crystallization, and the like.

In respect to Compound (I), there are two kinds of optical isomers due to their intramolecular asymmetric carbon atom.

Thus, when Compound (I) is obtained as a mixture of an i-isomer and a d-isomer, if desired, the mixture of the two isomers may be isolated respectively by per se known means of optical resolution such as resolution of disastereoisomers.

When Z in Compound (I) is hydrogen, Compound (I) may be isolated either as the free carboxylic acid or in the form of a pharmaceutically acceptable salt.

The free carboxylic acid may, after being isolated, be converted to a pharmaceutically acceptable salt. The pharmaceutically acceptable salt is exemplified by metal salts such as alkali metal salts, e.g. sodium and potassium salts, alkaline earth metal salts, e.g. magnesium and calcium salts, aluminum salt, and amine salts, e.g. ammonium, trimethylamine and triethylamine salts. Among these salts, the metal salts are particularly preferred.

Compound (I) which can thus be obtained is novel and has an excellent action to stabilize the lysosomal membranes of cells, and has vitamin-like activity, especially vitamin E-like activity and immunosuppressive activity, and accordingly is of use as, for example, immunosuppressive medicines and potentiators of immunosuppression.

Compound (I) is administered orally or non-orally, either as it is or in admixture with a suitable carrier, for example in such dosage forms as powders, granules, tablets and injections.

Pharmaceutical compositions containing one or more of Compound (I) and its salts can be prepared by per se conventional methods for the preparation of powder, capsules, tablets, granules, injections, and the like. The choice of carriers may be determined depending upon the route of administration, the solubility of the compounds and so on.

While the dosage of Compound (I) may be chosen depending upon the species of host, the purpose of administration and the route of administration, it is used, for the treatment of autoimmune diseases, for instance, ordinarily in the daily dose range for adult humans of about 0.1 to 0.5 grams by the oral route.

Schematically shown below are the reactions involved in the invention, inclusive of the processes for producing the starting compounds.

(wherein R's, OY, OY' and Z are as defined above; OY" is a hydroxyl group which may be protected.)

The advantageous protective group for OY" are acyloxy groups (e.g. acetoxy, etc.) and acetals (e.g. alpha-tetrahydropyranyloxy, etc.) and the like.

formed by procedures similar to those set forth in Process B. Depending upon the reaction conditions and the type of oxidizing agent, reaction of Process A also takes place in succession, giving rise to Compound (I). Particularly when, in Compound (IX), OY and OY' are

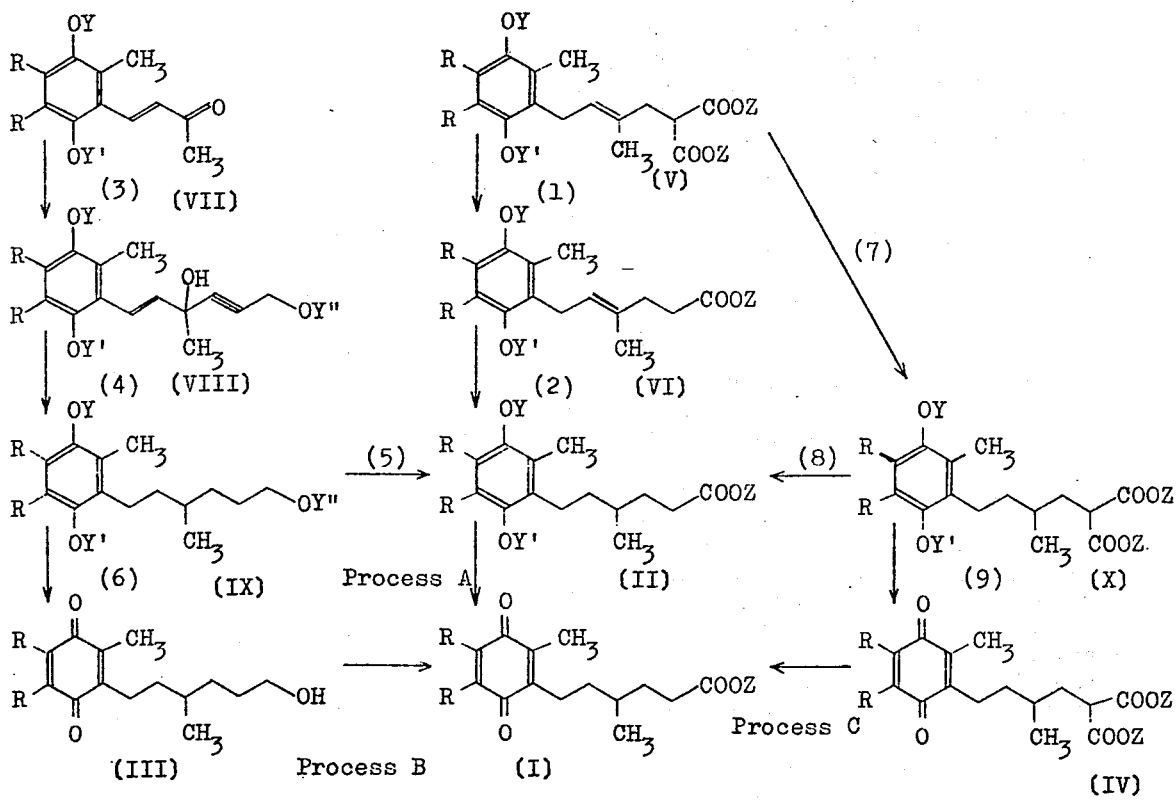

The step (1) is conducted by decarboxylating Compound (V), if desired, after hydrolysis of said compound. The decarboxylation and hydrolysis may be performed by procedures similar to those set forth above in connection with Process C.

The step (2) comprises reducing Compound (VI). The reduction may be carried out by per se known reduction means, catalytic reduction being particularly preferred. As the catalyst, palladium, platinum oxide or the like may be advantageously employed. The reaction is usually carried out at about 0°C to about 50°C, preferably about 15°C to about 30°C.

The step (3) comprises reacting Compound (VII) with a propargyl alcohol, either as such or after the hydroxyl group of propargyl alcohol has been protected. This reaction is conducted by a procedure which is conventional per se, and it is advantageous to employ a catalyst, examples of which are alkali metals such as metallic sodium, metallic lithium, etc. and lower alkyl-lithium such as n-butyl-lithium. Ordinarily the reaction is carried out in the presence of a suitable solvent, examples of which include ethers such as ethyl ether, tetrahydrofuran, dioxane, etc., liquid ammonia; etc. The reaction temperature is ordinarily about −80°C to about 50°C and, preferably, about −80°C to about 0°C.

The step (4) consists in reducing Compound (VIII). This reduction is performed by procedures similar to those set forth in the step (2).

The step (5) is conducted by oxidizing Compound (IX), if desired after hydrolysis. The oxidation is per-unprotected hydroxyl groups, the reaction of the step (5) is readily followed by the reaction of Process A. Further, following the reaction of the step (5), the reaction product may be first hydrolyzed by a procedure conventional per se and, then, subjected to the reaction of Process A, if desired.

The step (6) consists in oxidizing Compound [IX]. The oxidation is performed by procedures similar to those set forth in Process A.

Compound (III) also has an excellent action to stabilize lysosomal membranes, and shows vitamin-like activities, especially vitamin E-like activity, and immunosuppressive activity. Thus, they can be used as medicines in much the same manner as Compound [I].

The step (7) comprises reducing Compound (V). The reduction is performed by procedures similar to those set forth in the step (2).

The step (8) comprises decarboxylating Compound (X). This reaction may be conducted, if desired, after hydrolysis when Z in Compound (X) is a lower alkyl group. The decarboxylation and hydrolysis may be performed by procedures similar to those set forth above in connection with Process C.

The step (9) consists in oxidizing Compound (X). The oxidation is performed by procedures similar to those set forth in Process A. Compound (IV) also has an excellent activity to stabilize lysosomal membranes, and shows vitamin-like activities, especially vitamin E-like activity, and immunosuppressive activity and, as such, can be used as medicines in much the same manner as Compound [I].

The following Reference Examples and Examples are further illustrative of this invention. It should, of course, be understood that the scope of the invention is by no means limited by or to these examples.

Throughout the foregoing description as well as in the following Reference Examples, Examples and Claims, "°C", "N", "mg.", "g." and "ml." respectively denote "degrees centigrade", "Normal(s)", "milligram(s)" "gram(s)" and "milliliter(s)". The word "part(s)" is based on weight unless otherwise noted and the relationship between "part(s)" and "volume part(s)" corresponds to that between "gram(s)" and "milliliter(s)".

REFERENCE EXAMPLE 1

10.5 Parts of 4-acetoxy-1-bromo-2-methyl-2-butene is added dropwise to a mixture of 1.0 part of sodium metal, 10.2 parts of diethyl malonate and 5.3 volume parts of benzene. After the dropwise addition has been completed, the mixture is stirred at 10°C for 1 hour and, following the addition of water, extracted with diethyl ether. The extract is washed with water, dried and evaporated to dryness under reduced pressure. The resultant residue is purified by column chromatography to obtain 6.17 parts of ethyl 4-acetoxy-2-methyl-2-butenylmalonate and 2.55 parts of ethyl 4-hydroxy-2-methyl-2-butenylmalonate. 1.74 part of ethyl 4-acetoxy-2-methyl-2-butenylmalonate and 1.09 part of 2,3,5-trimethylhydroquinone are dissolved in 30 volume parts of dioxane and warmed to 50°C–60°C. Then, under stirring in a current of nitrogen gas, a mixture of 5 volume parts of 47 % boron trifluoride-ethyl ether and 15 volume parts of dioxane is added dropwise. The reaction mixture is stirred for 4 hours and, following the addition of water, extracted with ether. The extract is washed with water, dried and evaporated to dryness under reduced pressure. The residue is dissolved in 30 volume parts of methanol and mixed under vigorous stirring with a 100 volume parts of 30 % solution of ferric chloride. The mixture is extracted with 500 volume parts of diethyl ether and the extract is washed with water, dried and distilled free of the solvent under reduced pressure. The residue is purified by chromatography on silicic acid and the fractions eluted with ether-hexane (1:19) are pooled and evaporated to dryness under reduced pressure. The described procedure gives 1.31 part of 2,3,5-trimethyl-6-(5',5'-diethoxycarbonyl-3'-methyl-2'-pentenyl)-1,4-benzoquinone (the quinone corresponding to Formula (V) wherein R=H$_3$C; OY, OY'=OH, Z=C$_2$H$_5$), as a yellowish oil.
Ultraviolet absorption spectrum $\lambda_{max}^{EtOH}$m$\mu$ ($E_{1cm}^{1\%}$): oxidized form; 259.5 (448), 267(456); reduced form; 287.5 (108)
Infrared absorption spectrum $\nu_{max}^{film}$ cm$^{-1}$: 1740(COOC$_2$H$_5$), 1650(quinone)
Nuclear magnetic resonance spectrum ($\tau$ in deuterochloroform): 8.77(CH$_3$, triplet), 8.35(cis-C=CCH$_3$, singlet), 8.26(trans-C=CCH$_3$, singlet), 8.02(ring CH$_3$, singlet), 7.46(trans-C=CCH$_2$, doublet), 7.24(cis-C=CCH$_2$, doublet), 6.86(ring CH$_2$, doublet),

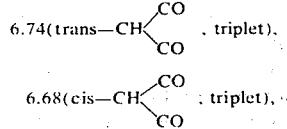

5.86(OCH$_2$, quartet), 5.00(C=CH, triplet) Elemental analysis, C$_{21}$H$_{28}$O$_6$; Calculated C, 67.00; H, 7.50; Found C, 67.01; H, 7.62.

A solution of 0.372 part of this product in 4 volume parts of ethanol is caused to absorb 2 molecular equivalents of hydrogen in the presence of platinum oxide. The catalyst is filtered off and the filtrate is evaporated to dryness under reduced pressure, whereupon 2,3,5-trimethyl-6-(5',5'-diethoxycarbonyl-3'-methylpentyl)-hydroquinone (Formula (X) wherein R=H$_3$C; OY, OY'=OH; Z=C$_2$H$_5$) is obtained as a pale yellowish oil. To a diethyl ether solution of this product is added 5 volume parts of 30 % potassium hydroxide containing 5 % of hydrosulfite and the mixture is stirred in a current of nitrogen gas for 2 hours. The water layer is rendered acidic with dilute hydrochloric acid and extracted with ether. The ethereal extract is washed with water, dried and evaporated to dryness under reduced pressure. The described procedure gives 0.2 part of 2,3,5-trimethyl-6-(5',5'-dicarboxy-3'-methylpentyl) hydroquinone (Formula (X) wherein R=H$_3$C, OY, OY'=OH; Z=H) as a light-yellowish powder.

The above product is dissolved in 10 volume parts of a mixture of methanol and diethylether (1:1) and the solution is mixed well with 3 volume parts of a 50 % solution of ferric chloride. The reaction mixture is extracted with diethyl ether and the extract is washed with water, dried and evaporated to dryness under reduced pressure. The residue is recrystallized from diethyl ether-hexane (1:1). The procedure gives 0.164 part of 2,3,5-trimethyl-6-(5',5'-dicarboxyl-3'methylpentyl)-1,4-benzoquinone (Formula (IV) wherein R=H$_3$C;Z=H) as light-yellowish needles melting at 110° – 112°C.

REFERENCE EXAMPLE 2

To a solution of 1.51 part of 1-acetoxy-4-hydroxy-2-methylnaphthalene, 1.4 part of 47 % boron trifluorideethyl ether and 0.35 part of zinc chloride in 26 volume parts of dioxane, there is added 1.21 part of ethyl 4-hydroxy-2-methyl-2-butenylmalonate in 20 volume parts of dioxane dropwise in a current of nitrogen gas at 50°C–60°°C with constant stirring. The reaction mixture is stirred for 5 hours and, following the addition of water, extracted with diethyl ether. The extract is washed with water, dried and evaporated to dryness, whereupon a yellowish oil is obtained. This product is chromatographed on a column of silicic acid and the fractions eluted with chloroform are evaporated to dryness under reduced pressure. The residue is recrystallized from diethyl ether-hexane. The procedure gives 0.55 part of 1-acetoxy-4-hydroxy-2-methyl-3-(5',5'-diethoxycarbonyl-3'-methyl-2'-pentenyl)naphthalene (Formula (V) wherein R=-CH=CH-CH=CH-; OY=O-COCH$_3$; OY'=OH; Z=C$_2$H$_5$) as light-brownish cubic crystals melting at 99.5°C–100.5°C.
Ultraviolet absorption spectrum $\lambda_{max}^{EtOH}$m$\mu$($E_{1cm}^{1\%}$):241(1297), 284(180)
Infrared absorption spectrum $\nu_{max}^{KBr}$cm$^{-1}$: 3500(OH),1760 and 1735 (OCOCH$_3$, COOC$_2$H$_5$)
Nuclear magnetic resonance spectrum ($\tau$ in deuterochloroform): 8.88(CH$_3$, triplet), 8.23(C=CCH$_3$, singlet), 7.85(ring CH$_3$, singlet), 7.55(COCH$_3$, singlet), 7.43(C=CCH$_2$, doublet), 6.80(ring CH$_2$, doublet),

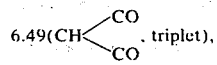

5.95(OCH$_2$, quartet), 4.85 (C=CH, triplet) 4.20(ring OH, singlet), 2.72-1.92 (ring protons, multiplet)

Elemental analysis, C$_{25}$H$_{30}$O$_7$; Calculated C, 67.85; H, 6.83; Found C, 67.80; H, 6.92.

This product is subjected to reduction, hydrolysis and oxidation in the same manner as Reference Example 1 to obtain 0.33 part of 2-methyl-3-(5',5'-dicarboxy-3'-methylpentyl)-1,4-naphthoquinone (Formula (IV) wherein R=-CH=CH-CH=CH-; Z=H) as a light-yellowish oil.

Nuclear magnetic resonance spectrum ($\tau$ in deuterochloroform): 8.93(CH$_3$, doublet), 8.75-8.02(CH$_2$CHCH$_2$, multiplet), 7.83(ring CH$_3$, singlet), 7.38(ring CH$_2$, triplet), 6.47(CH, triplet), 2.35, 2.00(ring protons, multiplet), 1.82(COOH, broad).

REFERENCE EXAMPLE 3

In 150 volume parts of dioxane are dissolved 3.64 parts of 2,3-dimethoxy-5-methylhydroquinone and 7.64 parts of ethyl 4-acetoxy-2-methyl-2-butenylmalonate and, under stirring in a current of nitrogen gas, 15 volume parts of 47 % boron trifluoride-ethyl ether and 120 volume parts of dioxane are added dropwise at 45°C–55°C. The mixture is stirred for 6 hours and, following the addition of water, extracted three times with diethyl ether. The extract is washed with water and evaporated to dryness to obtain a yellowish oil. This product is dissolved in 40 volume parts of methanol and the solution is mixed well with a solution of 50 parts of ferric chloride in 80 volume parts of water. The mixture is extracted with diethyl ether and the extract is mixed well with water, dried and distilled free of the solvent under reduced pressure. The residue is chromatographed on a column of silicic acid and eluted with chloroform. The eluate is further subjected to thin-layer chromatography with hexane-diethyl ether (1:1.) as the developer and from an orange-colored zone at Rf 0.33, there is obtained 3.12 parts of 2,3-dimethoxy-5-methyl-6-(5',5'-diethoxycarbonyl-3'-methyl-2'-pentenyl)-1,4-benzoquinone (the quinone corresponding to Formula (V) wherein R=H$_3$CO; OY, OY'=OH; Z=C$_2$H$_5$)

Ultraviolet absorption spectrum $\lambda_{max}^{EtOH}$ m$\mu$(E$_{1cm}^{1\%}$): oxidized form: 275 (359); reduced form: 291(131)

Infrared absorption spectrum $\nu_{max}^{film}$ cm$^{-1}$: 1750, 1735 (COOC$_2$H$_5$), 1665, 1650, 1615(quinone)

Nuclear magnetic resonance spectrum ($\tau$ in deuterochloroform): trans - 8.80(CH$_3$, triplet), 8.27(C=CCH$_3$, singlet), 8.04(ring CH$_3$, singlet), 7.47(C=CCH$_2$, doublet), 6.87(ring CH$_2$, doublet),

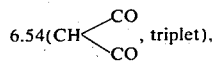

6.06 (OCH$_3$, singlet), 5.90(OCH$_2$, quartet), 5.02(C=CH, triplet); cis- 8.75(CH$_3$, triplet), 8.35 (C=CCH$_3$, singlet), 8.01(ring CH$_3$, singlet), 7.25 (C=CCH$_2$, doublet), 6.82(ring CH$_2$, doublet),

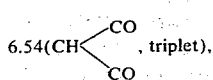

6.06(OH$_3$, singlet), 5.90(OCH$_2$, quartet), 5.02(C=CH, triplet)

Elemental analysis, C$_{21}$H$_{28}$O$_8$; Calculated C, 61.75; H, 6.91; Found C, 61.66; H, 6.92.

By procedures similar to those described in Reference Example 1, the above product is reduced, hydrolyzed and oxidized in the order mentioned to obtain 1.8 part of 2,3-dimethoxy-5-methyl-6-(5',5'-dicarboxy-3'-methylpentyl)-1,4-benzoquinone (Formula (IV) wherein R=H$_3$CO; Z=H) as an orange-yellowish oil.

Nuclear magnetic resonance spectrum ($\tau$ in deuterochloroform): 9.00(CH$_3$, doublet), 8.76–8.17(CH$_2$CHCH$_2$, multiplet), 8.02(ring CH$_3$, singlet), 7.55(ring CH$_2$, triplet), 6.48(CH, triplet), 6.07(OCH$_3$, singlet), 0.39 (COOH, broad)

REFERENCE EXAMPLE 4

10 Parts of 1,4-diacetoxy-2-(3'-oxo-1'-butenyl)-3,5,6-trimethylbenzene (Formula VII wherein R=CH$_3$; OY, OY'=OCOCH$_3$) in 2,500 volume parts of tetrahydrofuran is added dropwise to a mixture of a solution of 14 parts of 2-propargyloxytetrahydropyran in 1500 volume parts of tetrahydrofuran and a 15 % solution of n-butyl lithium in 65 volume parts of hexane. The entire mixture is stirred for 30 minutes and, following the addition of water, extracted with chloroform. The chloroform extract is washed with water, dried and evaporated to dryness. The residue is purified by chromatography on a column of silicic acid, whereupon 1,4-diacetoxy-2,3,5-trimethyl-6-[3'-hydroxy-3'-methyl-6'-($\alpha$-tetrahydropyranyloxy)-1'hexen-4'-ynyl]benzene (Formula (VIII) wherein R=H$_3$C; OY, OY'=OCOCH$_3$;

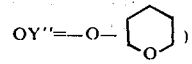

is obtained as a colorless oil. 4.35 Parts of this product is hydrogenated in 200 volume parts of methanol at atmospheric pressure with 2.5 parts of 5 % palladium-on-carbon. The catalyst is filtered off and a few drops of concentrated hydrochloric acid are added to the filtrate. The solution is stirred at 25°C for about 1 hour, after which time it is cooled to 0°C. The reaction mixture is extracted twice with 2000 volume parts portion each of ethyl acetate and the extract is treated in the routine manner to obtain a brown-colored oil. This oil is subjected to column chromatography on 120 parts of silica gel and elution is carried out with chloroform-acetone (10:1). The eluate is evaporated to dryness, whereupon 1,4-diacetoxy-2,3,5-trimethyl-6-(6'-hydroxy-3'methylhexyl)benzene (formula (IX) wherein R=H$_3$C; OY=OY'=OCOCH$_3$; OY''=OH) is obtained as a colorless oil.

Infrared absorption spectrum $\nu_{max}^{film}$ cm$^{-1}$: 3490(OH), 1760 (OCOCH$_3$)

Nuclear magnetic resonance spectrum ($\tau$ in deuterochloroform): 9.04 (side-chain CH$_3$, doublet), ~8.6 (CH$_2$, CH, broad), 8.21(OH, singlet), 7.97(COCH$_3$, singlet), 7.93 (ring CH$_3$, singlet), 7.68 (ring CH$_3$, singlet), 7.6 (ring CH$_2$, triplet), 6.4(OCH$_2$, triplet)

Mass spectrum (m/e): 350(molecular ion peak), 308, 266(molecular ion peak-2COCH$_3$+2), 207, 165

1.7 Part of this product is dissolved in 450 volume parts of 67 % methanol containing 300 parts of hydrosulfite and, following the addition of 500 volume parts of 10 % KOH, the solution is stirred for 30 minutes. To the reaction mixture 1000 volume parts of water is added and, after neutralization with 3N hydrochloric acid, the mixture is extracted with ethyl acetate. The solvent is distilled off and the residue is dissolved in 67 % methanol, followed by the addition of a solution of ferric chloride. The mixture is stirred for 20 minutes and, after being diluted with 1000 volume parts of water, it is extracted with ethyl acetate. The solvent is distilled off and the residue is purified by column chromatography. The procedure gives 6.67 parts of 2,3,5-trimethyl-6-(6′-hydroxy-3′-methylhexyl)-1,4-benzoquinone (formula (III) wherein R=H$_3$C) as an orange-yellowish oil.

Infrared absorption spectrum $\nu_{max}^{film}$ cm$^{-1}$: 3400(OH), 1640(quinone)

Nuclear magnetic resonance spectrum ($\tau$ in carbon tetrachloride): 9.06(CH$_3$, doublet), 8.9-8.2(3CH$_2$, CH, multiplet), 8.06(3 ring CH$_3$, singlet), 7.60(ring CH$_2$, triplet), 7.32(OH, singlet), 6.46(OCH$_2$, multiplet)

Mass spectrum (m/e): 264 (molecular ion peak)

REFERENCE EXAMPLE 5

A mixed solution of 10 parts of 1,4-diacetoxy-3-formyl-2-methylnaphthalene and 20 parts of 2-oxo-1-propylidenetriphenylphosphoran in 1000 volume parts of dioxane is stirred under reflux for 1.5 hour, after which it is evaporated to dryness. The residue is purified by chromatgraphy on a column of silicic acid. The described procedure gives 1,4-diacetoxy-2-methyl-3-(3′-oxo-1′-butenyl)naphthalene (Formula (VII) wherein R=-CH=CH-CH=CH-; OY, OY′=OCOCH$_3$) as colorless needles. 1.55 Part of this product is reacted with 2.41 parts of 2-propargyloxytetrahydropyran, catalytically reduced and hydrolyzed in the same manner as Reference Example 4.

In this manner, there is obtained a colorless oil of 1,4-diacetoxy-2-methyl-3-(6′-hydroxy-3′-methylhexyl)naphthalene (Formula (IX) wherein R=-CH=CH-CH=CH-, OY, OY′=OCOCH$_3$; OY″=OH).

Infrared absorption spectrum $\nu_{max}^{film}$ cm$^{-1}$: 3400(OH), 1760(OCOCH$_3$)

Nuclear magnetic resonance spectrum ($\tau$ in deuterochloroform): 9.0(side-chain CH$_3$, doublet), ~8.5 (CH$_2$, CH, broad), 7.72(ring CH$_3$, singlet) 7.54(COCH$_3$, singlet), 7.3(ring CH$_2$, multiplet), 6.4(OCH$_2$ multiplet), 2.4(ring H, multiplet)

Mass spectrum (m/e): 372(molecular ion peak), 330, 288(molecular ion peak-2COCH$_3$+2), 229, 187

0.01 Part of this product is hydrolyzed and, then, oxidized in the same manner as Reference Example 4, whereupon 0.009 part of 2-methyl-3-(6′-hydroxy-3′-methylhexyl)-1,4-naphthoquinone (Formula (III) wherein R=-CH=CH-CH=CH-; is obtained as a light-yellowish oil.

Ultraviolet absorption spectrum $\lambda_{max}^{EtOH}$ m$\mu$: 244,248,265,272

Infrared absorption spectrum $\nu_{max}^{film}$ cm$^{-1}$: 3400(OH), 1660(quinone)

Nuclear magnetic resonance spectrum ($\tau$ in deuterochloroform): 9.0(CH$_3$, doublet), 8.8 ~8.1(CH$_2$, CH, multiplet), 7.8(ring CH$_3$, singlet), 7.5 (ring CH$_2$, triplet), 6.4(CH$_2$O, triplet), 2.1~2.5 (ring H, multiplet), 1.7~2.1(ring H, multiplet).

REFERENCE EXAMPLE 6

A mixture of 6 parts of 1,4-diacetoxy-2,3-dimethoxy-6-formyl-5-methylbenzene, 12 parts of 2-oxo-1-propylidenetriphenylphosphoran and 500 volume parts of dioxane is stirred under reflux for 17 hours and the reaction mixture is evaporated to dryness. The residue is purified by chromatography on a column of silica gel, whereupon 1,4-diacetoxy-2,3-dimethoxy-5-methyl-6-(3′-oxo-1′-butenyl)-benzene (Formula (VII) wherein R=OCH$_3$; OY, OY′=OCOCH$_3$) is obtained as a brown oil. 2 Parts of this product is reacted with 2.77 parts of 2-propargyloxytetrahydropyran, reduced catalytically and hydrolyzed in the same manner as Reference Example 4. The described procedure gives 1,4-diacetoxy-2,3-dimethoxy-5-methyl-6-(6′-hydroxy-3′-methylhexyl)benzene (Formula (IX) wherein R=OCH$_3$; OY, OY′=OCOCH$_3$; OY″=OH) as a colourless oil.

Nuclear magnetic resonance spectrum ($\tau$ in deuterochloroform): 9.05 (side-chain CH$_3$, doublet), ~8.5(CH$_2$, CH, broad), 7.94(ring CH$_3$, singlet), 7.68(COCH$_3$ singlet), ~7.5(ring CH$_2$, multiplet), 6.4(OCH$_2$, multiplet), 6.18(OCH$_3$, singlet)

0.01 Part of this product is hydrolyzed and oxidized in the order mentioned as in Reference Example 4 to obtain 0.008 part of 2,3-dimethoxy-5-methyl-6-(6′-hydroxy-3′-methylhexyl)-1,4-benzoquinone (Formula [III] wherein R=OCH$_3$) as an orange-colored oil.

Ultraviolet absorption spectrum $\lambda_{max}^{EtOH}$ m$\mu$: 278

Infrared absorption spectrum $\lambda_{max}^{film}$ cm$^{-1}$: 3450 (OH), 1665, 1650, 1615 (quinone)

Nuclear magnetic resonance spectrum ($\tau$ in deuterochloroform): 9.03 (CH$_3$, doublet), 8.87~8.17(CH$_2$, CH, multiplet), 8.00(ring CH$_3$, singlet), 7.87(OH broad), 7.54 (ring CH$_2$, triplet), 6.36(CH$_2$O, triplet), 6.02(H$_3$CO, singlet).

EXAMPLE 1

In 40 volume parts of ethanol is dissolved 3.72 parts of 2,3,5-trimethyl-6-(5′,5′-diethoxycarbonyl-3′-methyl-2′-pentenyl)-1,4-benzoquinone(the quinone corresponding to Formula (V) wherein R=H$_3$C; OY, OY′λ =OH; Z=C$_2$H$_5$) obtained in Reference Example 1 and the solution is caused to absorb two molecular equivalents of hydrogen in the presence of platinum oxide. The catalyst is filtered off and the filtrate is evaporated to dryness under reduced pressure, whereupon 2,3,5-trimethyl-6-(5′,5′-diethoxycarbonyl-3′-methylpentyl)-hydroquinone (Formula (X) wherein R=H$_3$C; OY, OY′=OH; Z=C$_2$H$_5$) is obtained as a pale yellowish oil. To a diethyl ether solution of this product is added 50 volume parts of 30 % potassium hydroxide containing 5 % of hydrosulfite and the mixture is stirred in a current of nitrogen gas for 2 hours.

The water layer is rendered acidic with dilute hydrochloric acid and extracted with diethyl ether. The ethereal extract is washed with water and dried. The solvent is evaporated under reduced pressure to dryness, whereupon 2,3,5-trimethyl-6-(5′,5′-dicarboxy-3′-methylpentyl) hydroquinone (Formula (X) wherein R=H$_3$C; OY, OY′=OH; Z=H) is obtained as a light yellowish powder. This product is decarboxylated by heating at 150°C–160°C for 30 minutes and the reaction product is dissolved in 100 volume parts of a mixture of methanol-ether (1:1). The solution is mixed well with 20 volume parts of 50 % aqueous solution of ferric chloride. The reaction mixture is extracted twice with 100 volume parts of diethyl ether, and the extract is washed with water and dried, followed by evaporation to dryness under reduced pressure. The procedure gives a yellowish oil. This product is chromatographed on a column of 20 parts of silicic acid and elution is carried out with chloroform. In this manner 1.31 part of 2,3,5-trimethyl-6-(5'-carboxy-3'-methylpentyl)-1,4-benzoquinone (Formula (I) wherein R=$H_3C$; Z=H) is obtained as a yellowish oil.

Ultraviolet absorption spectrum $\lambda_{max}^{EtOH}$ m$\mu$: 261, 268.5

Infrared absorption spectrum $\nu_{max}^{film}$ cm$^{-1}$: ~2650, 1710 (COOH), 1640(quinone)

Nuclear magnetic resonance spectrum ($\tau$ in deuterochloroform): 9.01($CH_3$, doublet), 8.82~8.20($CH_2CHCH_2$, multiplet), 8.04(ring $CH_3$, singlet), 7.74~7.50(ring $CH_2$, $CH_2CO$, multiplet), -1.12(COOH, broad)

The yellowish oil is left standing for 24 hours at 3°C, and the crystals then produced are recrystallized from ligroine to give 1.0 part of yellowish needles melting at 58.5°C–61°C.

EXAMPLE 2

To 3.74 parts of 2,3,5-trimethyl-6-(5',5'-diethoxycarbonyl-3'-methyl-2'-pentenyl)-1,4-benzoquinone obtained in Reference Example 1(the quinone corresponding to Formula (V) wherein R=$H_3C$; OY, OY'$\lambda$=OH, Z=$C_2H_5$) in 100 volume parts of diethyl ether is added 40 volume parts of 20 % aqueous hydrosulfite solution under stirring in a current of nitrogen gas and the mixture is stirred for 1 hour. Then, 50 volume parts of 30 % potassium hydroxide is added, followed by stirring at room temperature for 1 hour. After the reaction, the mixture is extracted with diethyl ether and the ethereal layer is washed with water. The water is pooled with the aqueous washings and the mixture is rendered acidic with dilute hydrochloric acid, followed by extraction with two portions of diethyl ether. The extracts are pooled, washed with water and dried. Removal of the solvent by distillation leaves 2,3,5-trimethyl-6-(5',5'-dicarboxy-3'-methyl-2'-pentenyl)-hydroquinone (Formula (V) wherein R=$H_3C$;OY, OY'=OH; Z=H) as a pale yellowish powder. This product is decarboxylated by heating at 145°C – 155°C for 1 hour. The reaction product is dissolved in 80 volume parts of ethanol and the solution is caused to absorb 1 mole equivalent of hydrogen in the presence of platinum oxide. The catalyst is filtered off and the filtrate is mixed well with 100 volume parts of 40 % aqueous solution of ferric chloride. The reaction product is extracted with diethyl ether and the extract is washed with water, dried and evaporated to dryness under reduced pressure. The residue is chromatographed on a column of silicic acid and elution is carried out with chloroform. The procedure gives 0.97 part of 2,3,5-trimethyl-6-(5'-carboxy-3'-methylpentyl)-1,4-benzoquinone (Formula (I) wherein R=$H_3C$; z=H) as a yellowish oil.

The yellowish oil is left standing for 24 hours at 3°C, and the crystals then produced are recrystallized from ligroine to give 0.9 part of yellowish needles melting at 58.5° – 61°C.

EXAMPLE 3

2.2 Parts of 1-acetoxy-4-hydroxy-2-methyl-3-(5',5'-diethoxycarbonyl-3'-methyl-2'-pentenyl)naphthalene (Formula (V) wherein R=-CH=CH-CH=CH-; OY=OCOCH$_3$, OY'=OH; Z=$C_2H_5$) obtained in Reference Example 2 is treated in the same manner as Example 1 to obtain 0.5 part of 2-methyl-3-(5'-carboxy-3'-methylpentyl)-1,4-naphthoquinone (Formula (I) wherein R=-CH=CH-CH=CH-; Z=H) as light yellowish needles, melting point 61.5° – 63°C.

Ultraviolet absorption spectrum $\lambda_{max}^{KBr}$ (in ethanol containing 1 % of 1M ammonium acetate buffer (pH 5)) m$\mu$ (E$_{1cm}^{1\%}$); oxidized form: 244 (560), 248(570), 265(552); 272 (580), 330(87), reduced form: 244.5 (1380), 323(140), 333 (140)

Infrared absorption spectrum $\lambda_{max}^{KBr}$ cm$^{-1}$: ~2500, 1705 (COOH), 1655, 1620(quinone), 1595(aromatic nucleus)

Nuclear magnetic resonance spectrum ($\tau$ in deuterochloroform): 9.00($CH_3$, doublet), 8.75~8.22($CH_2CHCH_2$, multiplet), 7.84(ring $CH_3$, singlet, 7.70~7.25 (ring $CH_2$, $CH_2CO$, multiplet), 2.40~1.80(ring protons, multiplet), -0.67 (COOH, broad)

analysis, $C_{18}H_{20}O_4$; Calculated C, 71.98; H, 6.71; Found C, 71.96; H, 6.80.

EXAMPLE 4

2.2 Parts of 1-acetoxy-4-hydroxy-2-methyl-3-(5',5'-diethoxycarbonyl-3'-methyl-2'-pentenyl)naphthalene (Formula (V) wherein R=-CH=CH-CH=CH-; OY=OCOCH$_3$, OY'=OH; Z=$C_2H_5$) obtained in Reference Example 2 is treated in the same manner as Example 2 to obtain 0.5 part of 2-methyl-3-(5'-carboxy-3'-methylpentyl)-1,4-naphthoquinone (Formula (I) wherein R=-CH=CH-CH=CH-; Z=H) as light yellowish needles.

EXAMPLE 5

1.4 Part of 2,3-dimethoxy-5-methyl-6-(5',5'-diethoxycarbonyl-3'-methyl-2'-pentenyl)-1,4-benzoquinone (the quinone corresponding to Formula (V) wherein R=$H_3CO$; OY, OY'=OH; Z=$C_2H_5$) obtained in Reference Example 3 is treated in the same manner as Example 1 to obtain 0.4 part of 2,3-dimethoxy-5-methyl-6-(5'-carboxy-3'-methylpentyl)-1,4-benzoquinone (Formula (I) wherein R=$H_3CO$; Z=H) as an orange-colored oil.

Ultraviolet absorption spectrum $\lambda_{max}^{EtOH}$ m$\mu$ (E$_{1cm}^{1\%}$): oxidized form: 278(532); reduced form: 290(175)

Infrared absorption spectrum $\nu_{max}^{film}$ cm$^{-1}$: ~2500, 1740, 1708(COOH), 1665, 1650, 1615(quinone)

Nuclear magnetic resonance spectrum ($\tau$ in deuterochloroform): 9.02($CH_3$, doublet), 8.80~8.27 ($CH_2CHCH_2$, multiplet), 8.00(ring $CH_3$, singlet), 7.75~7.42 (ring $CH_2$, $CH_2CO$, multiplet), 6.03 (OCH$_3$, singlet), 1.27 (COOH, broad)

Elemental analysis, $C_{16}H_{22}O_6$; Calculated C, 61.92; H, 7.15; Found C, 61.72; H, 7.21.

EXAMPLE 6

3.2 Parts of 2,3-dimethoxy-5-methyl-6-(5',5'-diethoxycarbonyl-3'-methyl-2'-pentenyl)-1,4-benzoquinone (the quinone corresponding to Formula (V) wherein R=$H_3CO$; OY, OY'=OH; Z=$C_2H_5$) obtained in Reference Example 3 is treated in the same manner as Example 2 to obtain 0.8 part of 2,3-dimethoxy-5-methyl-6-(5'-carboxy-3'-methylpentyl)-1,4-benzoquinone (Formula (I) wherein R=$H_3CO$; Z=H) as an orange-colored oil.

EXAMPLE 7

Under stirring at 0°C, to 2.75 parts of 1,4-diacetoxy-2,3,5-trimethyl-6-(6'-hydroxy-3'-methylhexyl)benzene (Formula (IX) wherein R=H₃C- ; OY, OY'=OCOCH₃: OY''=OH) obtained in Reference Example 4 in 50 volume parts of acetone is added dropwise 5 volume parts of a 26 % solution of chromium trioxide in dilute sulfuric acid. The mixture is stirred for 1 hour, after which time the reaction mixture is extracted with 150 volume parts of ethyl acetate. The extract is then evaporated to dryness to obtain a white powder of 1,4-diacetoxy-2,3,5-trimethyl-6-(5'-carboxy-3'-methylpentyl)benzene (Formula (II) wherein R=H₃C; OY', OY=OCOCH₃; Z=H). This product is dissolved in 30 volume parts of methanolwater (2:1) and, then, 2 parts of hydrosulfite is added. Under stirring in a current of nitrogen gas, 100 volume parts of 10 % potassium hydroxide is added dropwise and the mixture is stirred for 5 hours. The reaction mixture is rendered acidic with hydrochloric acid and extracted with ethyl acetate. The extract is washed with water, dried and evaporated to dryness. The residue is dissolved in 30 % aqueous methanol and the solution is mixed under vigorous stirring with a solution of 30 parts of ferric chloride in 100 volume parts of 30 % aqueous methanol. Following the addition of water, the mixture is extracted with diethyl ether and the extract is washed with water dried and evaporated to dryness. The residue is purified by chromatography on a column of silicic acid. The procedure gives 1.3 part of 2,3,5-trimethyl-6-(5'-carboxy-3'-methylpentyl)-1,4-benzoquinone (Formula (I) wherein R=H₃C; Z=H) as a yellowish oil.

The yellowish oil is left standing for 24 hours at 3°C., and the crystals then produced are recrystallized from ligroine to give 1.0 part of yellowish needles melting at 58.5°–61°C.

EXAMPLE 8

5.2 parts of 1,4-diacetoxy-2-methyl-3-(6'-hydroxy-3'-methylhexyl)naphthalene (Formula (IX) wherein R=-CH=CH-CH=CH-; OY, OY'=OCOCH₃, OY'λ'=OH) obtained in Reference Example 5 is oxidized, hydrolyzed and oxidized in the same manner as Example 7 to obtain 4.2 parts of 2-methyl-3-(5'-carboxy-3'-methylpentyl)-1,4-naphthoquinone (Formula (I) wherein R=-CH=CH-CH=CH-; Z=H) as yellowish needles.

EXAMPLE 9

In 100 volume parts of methanol, 1.46 part of 2,3,5-trimethyl-6-(3'-methyl-5'-methoxycarbonyl-2'-pentenyl)-1,4-benzoquinone (the quinone corresponding to Formula (VI) wherein R=H₃C; OY, OY'=OH, Z=CH₃) is stirred in a current of hydrogen in the presence of platinum oxide, whereby the solution is caused to absorb the hydrogen. Thereafter, the catalyst is filtered off and a solution of 10 parts of ferric chloride in 100 volume parts of water is added. The mixture is stirred for 1 hour. Following the addition of water, the reaction mixture is extracted with diethyl ether and the extract is washed with water, dried over anhydrous sodium sulfate and distilled free of the solvent. The residue is dissolved in chloroform and purified by chromatography on a column of silicic acid. The described procedure gives 1.03 part of 2,3,5-trimethyl-6-(3'-methyl-5'-methoxycarbonylpentyl)-1,4-benzoquinone (Formula (I) R=CH₃, Z=CH₃) as a yellowish oil.
Infrared absorption spectrum $\nu_{max}^{film}$ cm⁻¹: 1740(COOCH₃), 1640(quinone)
Nuclear magnetic resonance spectrum (τ in deuterochloroform): 9.00(CH₃, doublet), 8.8~8.2(CH₂CHCH₂, multiplet), 8.00 (ring CH₃, singlet), 7.9~7.2(ring CH₂, CH₂COO, multiplet), 6.32(COOCH₃, singlet)
Elemental analysis, C₁₇H₂₄O₄; Calculated C, 69.83; H, 8.27; Found C, 69.83; H, 8.37.

EXAMPLE 10

8 Parts of 1,4-diacetoxy-2,3-dimethoxy-5-methyl-6-(6'-hydroxy-3'-methylhexyl)benzene (Formula (IX) wherein R=OCH₃; OY, OY'=OCOCH₃; OY''=OH) obtained in Reference Example 6 is oxidized, hydrolyzed and oxidized by precedures similar to those set forth in Example 7 to obtain 5 parts of 2,3-dimethoxy-5-methyl-6-(5'-carboxy-3'-methylpentyl)-1,4-benzoquinone (Formula (I) wherein R=OCH₃; Z=H) as an orange-colored oil.

EXAMPLE 11

4.3 Parts of 2,3,5-trimethyl-6-(5',5'-dicarboxy-3'-methylpentyl)-1,4-benzoquinone (Formula (IV) wherein R=H₃C; Z=H) obtained in Reference Example 1 is heated at 140°C for 1 hour. It is then subjected to thin-layer chromatography with chloroform-ethanol (19:1) as the developer and recrystallized from ligroine. Th described procedure gives 2.97 parts of 2,3,5-trimethyl-6-(5'-carboxy-3'-methylpentyl)-1,4-benzoquinone (Formula (I) wherein R=H₃C; Z=H) as yellowish needles. melting point 58°C–61°C.
Elemental analysis, C₁₆H₂₂O₄; Calculated C, 69.04; H, 7.97; Found C, 69.23; H, 8.18.

2.7 Parts of the thus-obtained 2,3,5-trimethyl-6-(5'-carboxy-3'-methylpentyl)-1,4-benzoquinone is dissolved in 85 volume parts of a 10 % aqueous solution of sodium bicarbonate, and the resulting solution is lyophilized to obtain 3.0 parts of 2,3,5-trimethyl-6-(5'-carboxy-3'-methylpentyl)-1,4-benzoquinone sodium salt.
Elemental analysis C₁₆H₂₁O₄Na; Calculated C, 63.98; H, 7.05; Found C, 63.21; H, 6.81.

EXAMPLE 12

2.2 Parts of 2-methyl-3-(5',5'-dicarboxy-3'-methylpentyl)-1,4-naphthoquinone (Formula (IV) wherein R=-CH=CH-CH=CH-, Z=H) obtained in Reference Example 2 is decarboxylated in the same manner as Example 11 to obtain 1.4 part of 2-methyl-3-(5'-carboxy-3'-methylpentyl)-1,4-naphthoquinone (Formula (I) wherein R=-CH=CH-CH=CH-; Z=H) as light-yellowish needles, melting point 61.5°C-63°C.
Elemental analysis, C₁₈H₂₀O₄; Calculated C, 71.98; H, 6.71; Found C, 72.14; H, 6.76

EXAMPLE 13

2.5 Parts of 2,3-dimethoxy-5-methyl-6-(5',5'-dicarboxy-3'-methylpentyl)-1,4-benzoquinone (Formula (IV) wherein R=CH₃O; Z=H) obtained in Reference Example 3 ; is decarboxylated in the same manner as Example 11 to obtain 1.13 part of 2,3-dimethoxy-5-methyl-6-(5'-carboxy-3'-methylpentyl)-1,4-benzoquinone (Formula (I) wherein R=H₃CO; Z=H) as an orange-colored oil.
Ultraviolet absorption spectrum $\nu_{max}^{EtOH}$ mμ ($E_1^{1\%}{}_{cm}$): oxidized form: 278(532); reduced form: 290(175)
Infrared absorption spectrum $\nu_{max}^{film}$ cm⁻¹: 2500, 1740, 1708(COOH), 1665, 1650, 1615(quinone)
Nuclear magnetic resonance spectrum (τ in deuterochloroform): 9.02(CH₃ doublet), 8.80~8.27(CH₂CHCH₂, multiplet), 8.00( ring CH₃, singlet), 7.75~7.42 ( ring CH₂, CH₂CO, multiplet), 6.03(CH₃O, singlet), 1.27(COOH, broad.)
Elemental analysis, $C_{16}H_{22}O_6$; Calculated C, 61.92; H, 7.15; Found C, 61.64; H, 7.30.

EXAMPLE 14

To 0.05 part of 2,3,5-trimethyl-6-(6'-hydroxy-3'-methylhexyl)-1,4-benzoquinone (Formula (III) wherein R=H₃C) obtained in Reference Example 4 in 300 volume parts of acetone is added, at 0°C, 10 volume parts of solution prepared by dissolving 267 parts of chromium trioxide in 230 volume parts of 98 % sulfuric acid and diluting the solution with water to make a total of 1000 volume parts. The mixture is stirred for 10 minutes and, following the dilution with 2000 volume parts of water extracted with 300 volume parts of diethyl ether. The solvent is distilled off and the residue is recrystallized from ligroine. The described procedure gives 0.05 part of 2,3,5-trimethyl-6-(5'-carboxy-3'-methylpentyl)-1,4-benzoquinone (Formula (I), wherein R=H₃C; Z=H) as yellowish needles melting at 58°C–61°C.

EXAMPLE 15

1.1 Part of 2-methyl-3-(6'-hydroxy-3-methylhexyl)-1,4-naphthoquinone (Formula (III) wherein R=CH=CH-CH=CH-) obtained in Reference Example 5 is oxidized in the same manner as Example 14 to obtain 0.8 part of 2-methyl-3-(5'-carboxy-3'-methylpentyl)-1,4-naphthoquinone (Formula (I) wherein R=CH=CH-CH=CH-; Z=H) as a light-yellowish needles, melting point; 61°C–63°C.

EXAMPLE 16

1.2 Part of 2,3-dimethoxy-5-methyl-6-(6'-hydroxy-3'-methylhexyl)-1,4-benzoquinone (Formula (III) wherein R= OCH₃) obtained in Reference Example 6 is oxidized in the same manner as Example 14 to obtain 1.0 part of 2,3-dimethoxy-5-methyl-6-(5'-carboxy-3'-methylpentyl)-1,4-benzoquinone (Formula (I) wherein R=CH₃O; Z=H) as an orange-colored oil.

EXAMPLE 17

To 10 parts of 2,3,5-trimethyl-6-(5'-carboxy-3'-methylpentyl)-1,4-benzoquinone (Formula (I) wherein R=H₃C; Z=H) in 1000 volume parts of diethyl ether is added 7500 volume parts of ethereal solution containing 28 % of diazomethane. After the evolution of nitrogen gas has subsided, the solvent is distilled off and the residue is purified by chromatography on silicic acid. The procedure gives 10 parts of 2,3,5-trimethyl-6-(3'-methyl-5'-methoxycarbonylphenyl)-1,4 -benzoquinone (Formula (I) wherein R=H₃C;Z=CH₃) as a yellowish oil.
Infrared absorption spectrum $\nu_{max}^{film}$ cm⁻¹: 1740(COOCH₃), 1640(quinone)
Nuclear magnetic resonance spectrum( τ in deuterochloroform): 9.00(CH₃, doublet), 8.8~8.2(CH₂CHCH₂, multiplet), 8.00 ( ring CH₃, singlet), 7.9~7.2( ring CH₂, CH₂COO, multiplet), 6.32(COOCH₃, singlet)
Elemental analysis, $C_{17}H_{24}O_4$; Calculated C, 69.83; H, 8.27; Found C, 69.79; H, 8.34.

By procedures similar to those described in the foregoing Examples, the following compounds are prepared:
2,3-diethyl-5-methyl-6-(5'-carboxy-3'-methylpentyl)-1,4-benzoquinone.
2,3-di-n-propyl-5-methyl-6-(5'-carboxy-3'-methylpentyl)-1,4-benzoquinone.
2,3-diethoxy-5-methyl-6-(5'-carboxy-3'-methylpentyl)-1,4-benzoquinone.
2,3-diisopropoxy-5-methyl-6-(5'-carboxy-3'-methylpentyl)-1,4-benzoquinone.
2,3,5-trimethyl-6-(5'-propoxycarbonyl-3'-methylpentyl)-1,4-benzoquinone.
2,3,5-trimethyl-6-(5'-carboxy-3'-methylpentyl)-1,4-benzoquinone ammonium salt.
2,3-dimethoxy--5-methyl-6-(5'-carboxy-3'-methylpentyl)-1,4-benzoquinone magnesium salt.
2,3,5-trimethyl-6-(5'-isopropoxycarbonyl-3'-methylpentyl)-1,4-benzoquinone.

EXAMPLE 18

Some examples of practical recipes in which a quinone derivative of this invention is utilized for the treatment of the autoimmune diseases are as follow:

A (Capsule)
| | | |
|---|---|---|
| (1) | 2,3-dimethoxy-5-methyl-6-(5'-carboxyl-3'-methylpentyl)-1,4-benzoquinone | 20 mg. |
| (2) | Corn oil | 150 mg. |
| | | 170 mg. per capsule |

(1) is added to (2), and then heated to about 40°C to dissolve (1) in (2). The whole is filled into a gelatin capsule.

B (Injection)
| | | |
|---|---|---|
| (1) | 2,3,5-trimethyl-6-(5'carboxy-3'-methylpentyl)-1,4-benzoquinone | 10 mg. |
| (2) | Sodium bicarbonate | 3 mg. |
| (3) | Sodium chloride | 0.018 mg. |

(1) is dissolved in 1.5 ml. of aqueous solution containing (2), to which (3) is added, then water is supplemented to make the whole volume 2.0 ml.

What we claim is:
1. A compound selected from the group consisting of compounds of the formula

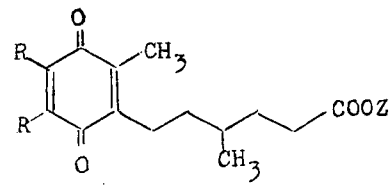

wherein R represents lower alkyl or lower alkoxy, or the R groups taken together form -CH=CH-CH=CH-, and Z represents hydrogen or lower alkyl, and pharmaceutically acceptable salts thereof.

2. A compound is claimed in claim 1, wherein each R is lower alkyl.

3. A compound as claimed in claim 1, wherein each of R is lower alkoxy.

4. A compound as claimed in claim 1, wherein the R groups taken together form -CH=CH-CH=CH-.

5. A compound as claimed in claim 1, wherein Z is hydrogen.

6. A compound as claimed in claim 1, wherein Z is lower alkyl.

7. A compound as claimed in claim 1, wherein each R is lower alkyl and Z is hydrogen.

8. A compound as claimed in claim 1, wherein each R is lower alkoxy and Z is hydrogen.

9. A compound as claimed in claim 1, wherein the R groups taken together form -CH=CH-CH=CH- and Z is hydrogen.

10. A compound as claimed in claim 1, wherein each R and Z is lower alkyl.

11. A compound as claimed in claim 1, in the form of a metal salt.

12. The compound as claimed in claim 1, wherein the compound is 2,3,5-trimethyl-6-(5'-carboxy-3'-methylpentyl)-1,4-benzoquinone.

13. The compound as claimed in claim 1, wherein the compound is 2,3-dimethoxy-5-methyl-6-(5'-carboxy-3'-methylpentyl)-1,4-benzoquinone.

14. The compound as claimed in claim 1, wherein the compound is 2-methyl-3-(5'-carboxy-3'-methylpentyl)-1,4-naphthoquinone.

15. The compound as claimed in claim 1, wherein the compound is 2,3,5-trimethyl-6-(5'-methoxycarbonyl-3'-methylpentyl)-1,4-benzoquinone.

* * * * *